(12) United States Patent
Angel

(10) Patent No.: US 7,131,951 B2
(45) Date of Patent: Nov. 7, 2006

(54) BIOPSY NEEDLE

(75) Inventor: Luis F. Angel, San Antonio, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 10/396,137

(22) Filed: Mar. 20, 2003

(65) Prior Publication Data

US 2004/0019297 A1    Jan. 29, 2004

Related U.S. Application Data

(60) Provisional application No. 60/365,989, filed on Mar. 20, 2002.

(51) Int. Cl.
*A61B 10/00* (2006.01)
(52) U.S. Cl. .................. 600/567; 600/562; 600/564
(58) Field of Classification Search ............ 600/562, 600/564–568, 570–571, 101, 104
See application file for complete search history.

(56) References Cited

U.S. PATENT DOCUMENTS

| 4,776,346 | A | * | 10/1988 | Beraha et al. | 600/567 |
| 4,791,937 | A | | 12/1988 | Wang | |
| 4,907,598 | A | * | 3/1990 | Bauer | 600/566 |
| 4,917,100 | A | * | 4/1990 | Nottke | 600/562 |
| 5,320,110 | A | | 6/1994 | Wang | |
| 5,458,112 | A | * | 10/1995 | Weaver | 600/566 |
| 5,560,373 | A | * | 10/1996 | De Santis | 600/566 |
| 5,562,102 | A | * | 10/1996 | Taylor | 600/564 |
| 5,578,030 | A | * | 11/1996 | Levin | 606/39 |
| 5,810,744 | A | * | 9/1998 | Chu et al. | 600/567 |
| 5,916,175 | A | * | 6/1999 | Bauer | 600/567 |
| 6,110,127 | A | * | 8/2000 | Suzuki | 600/565 |
| 6,193,673 | B1 | | 2/2001 | Viola et al. | |
| 6,261,243 | B1 | * | 7/2001 | Burney et al. | 600/564 |
| 6,514,215 | B1 | * | 2/2003 | Ouchi | 600/564 |
| 6,520,954 | B1 | * | 2/2003 | Ouchi | 606/1 |
| 6,572,563 | B1 | * | 6/2003 | Ouchi | 600/564 |

OTHER PUBLICATIONS

International Search Report for PCT/US03/08430 mailed Aug. 11, 2003.

* cited by examiner

*Primary Examiner*—Robert L. Nasser
*Assistant Examiner*—Patricia C. Mallari
(74) *Attorney, Agent, or Firm*—Meyertons, Hood, Kivlin, Kowert & Goetzel, P.C.; Eric B. Meyertons

(57) ABSTRACT

A biopsy needle assembly may include a sample needle, an actuator and a cutter. A sample needle may include a sample opening. A tissue sample may be positioned in the sample opening when the sample needle is inserted into tissue of a patient. The actuator may be activated to move the cutter relative to the sample needle and separate sample tissue in the sample opening from adjacent tissue. The biopsy needle assembly may be removed from the patient and the sample may be removed from the sample opening. In some embodiments, the sample needle may be inserted in tissue through an instrument (e.g., an endoscope). The biopsy needle assembly may include a sheath that inhibits a sample needle and a cutter from contacting the instrument when the biopsy needle is inserted in the instrument.

28 Claims, 5 Drawing Sheets

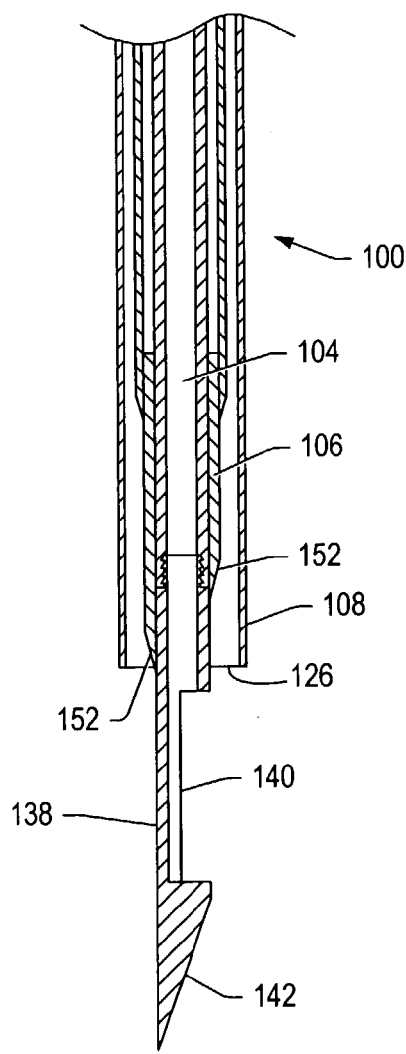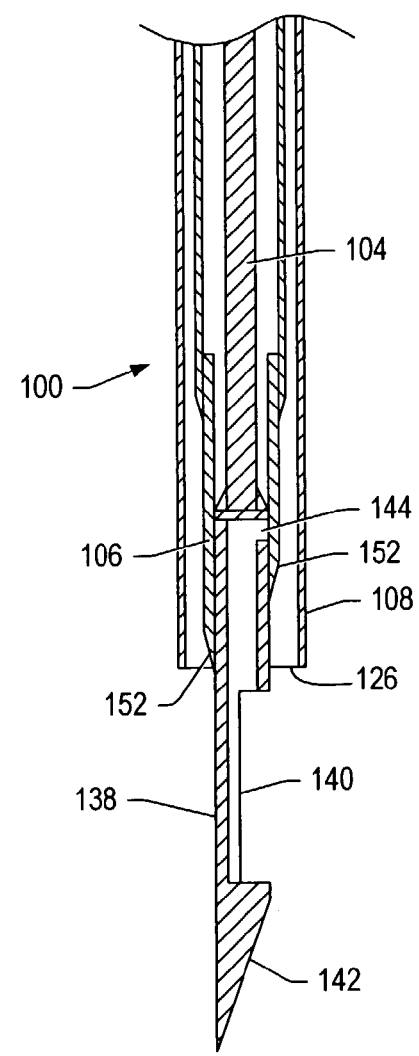
FIG. 3                    FIG. 4

BIOPSY NEEDLE

PRIORITY CLAIM

This application claims priority to Provisional Patent Application No. 60/365,989 entitled "BIOPSY NEEDLE" filed on Mar. 20, 2002.

BACKGROUND

1. Field of the Invention

The present invention generally relates to a biopsy needle for obtaining tissue samples. Embodiments of the invention relate to a biopsy needle for obtaining samples from within a patient through an endoscope or other instrument.

2. Description of Related Art

A biopsy procedure may be performed to determine if suspect cells are diseased or cancerous. The biopsy procedure may involve obtaining a tissue sample and/or body fluids from a patient. Tests performed on the tissue sample and/or body fluids may provide information for diagnosis of the patient's condition.

A biopsy sample may be obtained by invasive surgical procedures. For example, an incision may be made in a patient, a path to suspect cells may be formed by retraction and/or removal of tissue and a sample of suspect cells and/or biological material may be obtained. Less invasive procedures for obtaining biopsy samples may be used to obtain some biopsy samples. For example, a percutaneous biopsy may be performed using a needle-like instrument to collect a biopsy sample. To collect the biopsy sample using a percutaneous biopsy needle, a sharp portion of the biopsy needle may be used to puncture tissue to be sampled. The tissue sample may be collected in a hollow portion of the percutaneous biopsy needle.

Areas of a patient may be difficult to sample using an invasive surgical procedure or a percutaneous biopsy needle. To sample the areas, a biopsy needle may be guided to tissue to be sampled through an instrument positioned in a patient. The instrument may be, but is not limited to, an endoscope, conduit and/or medical device insertion instrument. The biopsy needle may be reciprocated in the instrument so that a stylet of the biopsy needle repeatedly enters into the tissue to be sampled. A biopsy sample may be obtained in a hollow portion of the stylet.

U.S. Pat. No. 4,791,937 to Wang, which is incorporated by reference as if fully set forth herein, describes a transendoscopic needle. The transendoscopic needle has an outer flexible catheter and a reciprocating interior structure on which the needle is mounted.

U.S. Pat. No. 5,320,110 to Wang, which is incorporated by reference as if fully set forth herein, describes a pleural biopsy syringe-needle. The pleural biopsy syringe-needle has two hollow inner and second guides whose proximal ends are directly attached to the barrel of a syringe. The syringe functions to reduce the probability of effecting pneumothorax in a patient during a pleural biopsy procedure.

SUMMARY

A biopsy needle assembly may be used to remove a tissue sample and/or biological material from a patient. The tissue sample may be tissue that is suspected of being cancerous and/or diseased. The biological material may be fluid. A retrieved tissue sample and/or retrieved biological material may be subjected to histological, cytological and/or other type of testing. The biopsy needle assembly may allow for the removal of the tissue sample without a need to reciprocate a needle into the tissue to be sampled.

An embodiment of a biopsy needle assembly may include an actuator, a sample needle and a cutter. The sample needle of the biopsy needle assembly may include a sample opening. A tissue sample may be positioned in the sample opening when the sample needle is inserted into tissue of a patient. The sample needle and the cutter may be coupled to the actuator. The sample needle may be positioned in the cutter. A needle section of the sample needle may be extended beyond a cutting portion of the cutter so that the needle section may be inserted into tissue that is to be sampled.

In an embodiment of a biopsy needle assembly, a portion of the sample needle may be a hollow conduit. A vacuum may be drawn through the portion of the sample needle to remove biological material from a patient and/or to seat a tissue sample into a sample opening of the sample needle.

In an embodiment of a biopsy needle assembly, the sample needle may include an opening in communication with a space between an inner surface of the cutter and an outer surface of the sample needle. A gasket or gaskets may be located between the opening and a sample opening of the sample needle. The gasket or gaskets may contact the inner surface of the cutter to inhibit passage of tissue or fluid through a distal end of the cutter. A vacuum may be drawn through the cutter to remove fluid and/or apply a vacuum to tissue through a needle portion of the sample needle.

An actuator of a biopsy needle assembly may move a cutter relative to a sample needle. In an embodiment of a biopsy needle assembly, an actuator extends a cutter so that the cutter moves relative to a sample needle. In an embodiment of a biopsy needle assembly, an actuator retracts a sample needle so that the sample needle moves relative to a cutter. In an embodiment of a biopsy needle assembly, an actuator may move both a cutter and a sample needle relative to the actuator to take a biopsy sample. When the actuator is engaged, the cutter moves relative to the sample needle so that the cutter separates a tissue sample positioned within a sample opening of the sample needle from adjacent tissue.

A biopsy needle assembly may be used to obtain a biopsy sample from a patient. The sample needle of the biopsy needle assembly may be positioned in tissue to be sampled so that the sample opening is in the tissue to be sampled. In some embodiments, a vacuum may be drawn through the sample needle to seat a sample within the sample opening. An actuator of the biopsy needle assembly may be activated to move a cutter relative to the sample needle so that the cutter separates the tissue sample from adjacent tissue. The biopsy needle assembly may be removed from the patient. The sample in the sample opening may be removed and tested.

Some embodiments of a biopsy needle assembly may include a sheath. The sheath of a biopsy needle assembly may attach to an actuator of the biopsy needle assembly. The position of the actuator relative to a first end of the sheath may be adjustable. When the actuator is in a first position relative to the first end of the sheath, a needle portion of a sample needle and a cutting edge of the cutter may be positioned within the sheath. When the actuator is in the first position relative to the first end of the sheath, the needle portion of the sample needle may be positioned in a patient without the needle portion or the cutter cutting edge coming into contact with tissue and/or with an instrument in which the biopsy needle assembly is inserted. When the actuator is in a second position relative to the first end of the sheath, a part of the needle portion may extend beyond a second end of the sheath so that the sample needle can be positioned into tissue to be sampled.

A sheath may be fixed in a position relative to an actuator when the actuator is in a first position. In an embodiment of a biopsy needle assembly, a detent of a sheath engages an opening in an actuator to fix the actuator in a first position. The actuator may be released from the first position and moved to a second position so that at least part of a needle portion of a sample needle extends beyond the sheath. The actuator may be fixed to the sheath when the actuator is in the second position. In some embodiments, a distance that part of a needle portion extends beyond a sheath may be a fixed distance when an actuator is fixed to the sheath in a second position. In other embodiments, a distance that part of a needle portion extends beyond a sheath may be adjustable. In an embodiment of an actuator, a portion of an actuator that couples to a sheath may be threadably connected to a body of the actuator. Adjustment of the threaded connection between the portion of the actuator and the body of the actuator may allow for adjustment of a distance that part of the needle portion extends beyond the sheath.

A sample needle of a biopsy needle assembly may have sufficient longitudinal strength to allow a needle portion to enter into tissue. Portions of the sample needle may be flexible to allow the sample needle to be placed at a desired location within a patient or within an instrument inserted in the patient. The flexibility of the sample needle allows the sample needle to follow curves of an instrument inserted into the patient so that the needle portion may be inserted into tissue to be sampled. The tissue sample may be located adjacent to an opening in the instrument. In some embodiments, a needle portion may include a tip made of a hardened material and a sharp material to facilitate insertion of the needle portion into tissue.

A cutter of a biopsy needle assembly may have sufficient longitudinal strength to allow a cutting edge of the cutter to separate tissue when an actuator of the biopsy needle assembly is activated. The cutter may be made of materials, or have coatings, that promote easy movement of the cutter relative to portions of a sample needle positioned within the cutter. Portions of the cutter may be flexible to allow the cutter to be placed at a desired location within a patient or within an instrument inserted in the patient. In some embodiments, a cutter may include a tip made of a hardened material and a sharp material to facilitate separation of tissue within a sample opening of the sample needle from adjacent tissue.

A sheath of a biopsy needle assembly may have sufficient strength to resist penetration by sharp portions of a cutter and/or a sample needle. The sheath may be flexible to allow a cutter and sample needle within the sheath to be placed at a desired location within a patient or within an instrument inserted in the patient. The sheath may be made of a material, or may include a coating, that promotes easy movement of a sample needle and a cutter relative to the sheath.

BRIEF DESCRIPTION OF THE DRAWINGS

Advantages of the present invention will become apparent to those skilled in the art with the benefit of the following detailed description of embodiments and upon reference to the accompanying drawings in which:

FIG. 3 depicts a cross-sectional representation of an embodiment of a distal portion of a biopsy needle assembly;

FIG. 4 depicts a cross-sectional representation of an embodiment of a distal portion of a biopsy needle assembly;

Figure 1:
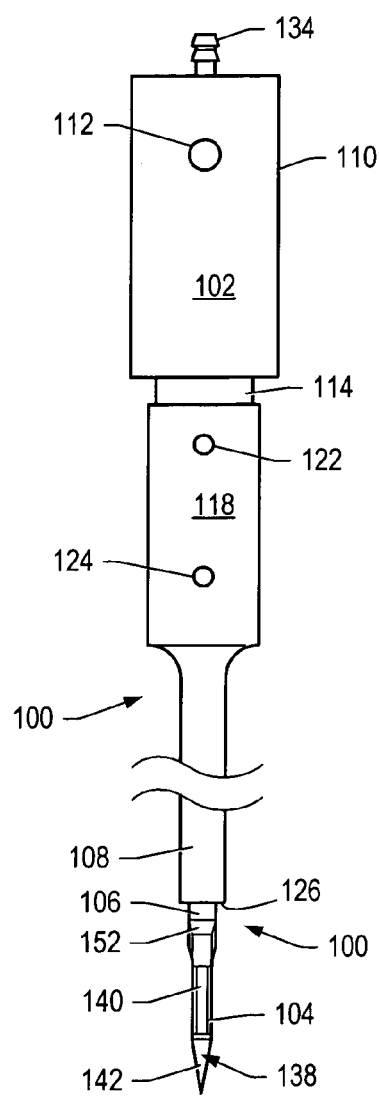
FIG. 1 depicts a side representation of an embodiment of a biopsy needle assembly.

While the invention is susceptible to various modifications and alternative forms, specific embodiments thereof are shown by way of example in the drawings and will herein be described in detail. The drawings may not be to scale. It should be understood that the drawings and detailed description thereto are not intended to limit the invention to the particular form disclosed, but to the contrary, the intention is to cover all modifications, equivalents and alternatives falling within the spirit and scope of the present invention as defined by the appended claims.

DETAILED DESCRIPTION OF EMBODIMENTS

Figure 2:
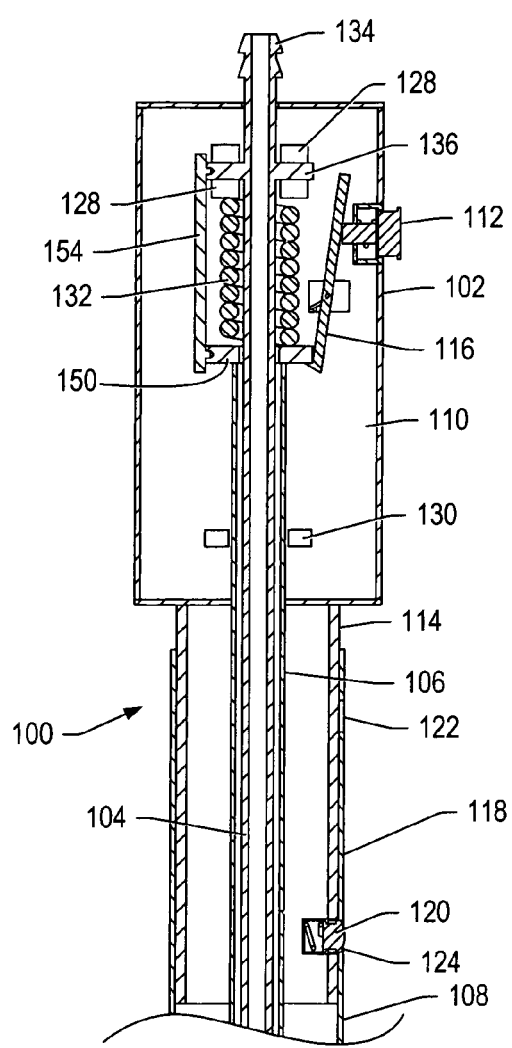
FIG. 2 depicts a cross-sectional representation of a proximal portion of an embodiment of an actuator of a biopsy needle assembly.

Referring to the drawings, particularly to FIG. 1 and FIG. 2, a biopsy needle assembly is designated generally by reference numeral 100. Biopsy needle assembly 100 may be used to obtain a tissue sample and/or biological material from a patient. Embodiments of biopsy needle assembly 100 may be used in conjunction with other instruments inserted in a patient to allow biopsy samples to be obtained from the patient. The instruments may be, but are not limited to, conduits, implant insertion tools and/or endoscopes. Other embodiments of biopsy needle assemblies may be used as stand-alone devices without the biopsy needle assembly being inserted through another instrument. Biopsy needle assembly components may be made of one material or of several different materials. Biopsy needle assembly components may include, but are not limited to, metals, polymers, glass and/or ceramics. Materials used to form biopsy needle assembly components may be provided as sterilized components and/or may be made of materials able to be autoclaved or chemically sterilized.

Some embodiments of biopsy needle assemblies may be used in conjunction with endoscopes. An endoscope is an instrument used to observe regions within a patient. Endoscopes and endoscopic procedures are often named for an organ or body region to be observed and/or treated. Examples of endoscopes and endoscopic procedures may include an endoscope inserted into, a gastrointestinal tract (alimentary tract endoscopy), a bladder (cystoscopy), an abdominal cavity (laparoscopy), a joint cavity (arthroscopy), a mid-portion of the chest (mediastinoscopy), a trachea (laryngoscopy) or a bronchial system (bronchoscopy). A biopsy needle assembly may be used to obtain a tissue sample from the region in which the endoscope is positioned and/or from an area adjacent to a region in which the endoscope is positioned. For example, a biopsy needle assembly inserted in a bronchoscope may be used to obtain a mediastinal biopsy sample. A length of a biopsy needle assembly may be dependent on the type of instrument that the biopsy needle assembly is to be used with and/or the location of tissue to be sampled. The length of a biopsy needle assembly may be from about 4 inches to about 30 inches. Longer or shorter lengths may also be used if desired.

Referring to FIG. 1, a biopsy needle assembly 100 may include actuator 102, sample needle 104, cutter 106 and sheath 108. Actuator 102 may include body 110, release 112 and sheath connection 114. In an embodiment of actuator 102, release 112 is a button in body 110.

FIG. 2 represents a cross-sectional view of a proximal section of an embodiment of an actuator of biopsy needle assembly 100. Actuator 102 may be coupled to sample needle 104 Actuator 102 may also be coupled to cutter 106. Sample needle 104 may be telescopically positioned within cutter 106. When actuator 102 is activated, cutter 106 moves relative to sample needle 104 so that a biopsy sample positioned in the sample needle is separated from adjacent tissue by the cutter.

Sheath 108 may inhibit contact of sample needle 104 and cutter 106 with tissue and/or an instrument during insertion or removal of the biopsy needle assembly 100 from a patient. Pushing release 112 may move lever arm 116 and allow movement of cutter 106 relative to sample needle 104. An outer surface of body 110 may be contoured so that a user is able to securely grasp actuator 102. In some actuator embodiments, a release is positioned to be activated by a finger or a thumb of a hand that grasps the actuator. In other actuator embodiments, a release is positioned to be activated by an opposite hand or by a different person than a person grasping the actuator.

Sheath connector 114 may be positioned in end portion 118 of an embodiment of sheath 108. Sheath connector 114 may include detent 120 or detents that engage edges of openings in sheath end portion 118. When detent 120 is in first sheath opening 122, sample needle 104 and cutter 106 may be positioned within sheath 108. When detent 120 is in second sheath opening 124, as depicted in FIG. 2, sample needle 104 may extend beyond end 126 (shown in FIG. 1) of sheath 108 so that the sample needle can be positioned in tissue to be sampled. In an actuator embodiment, an end portion of the actuator may include a keyway and a sheath connector may include a key to properly orient a detent relative to one or more sheath openings when the sheath connector is inserted into a sheath.

Figure 2A:
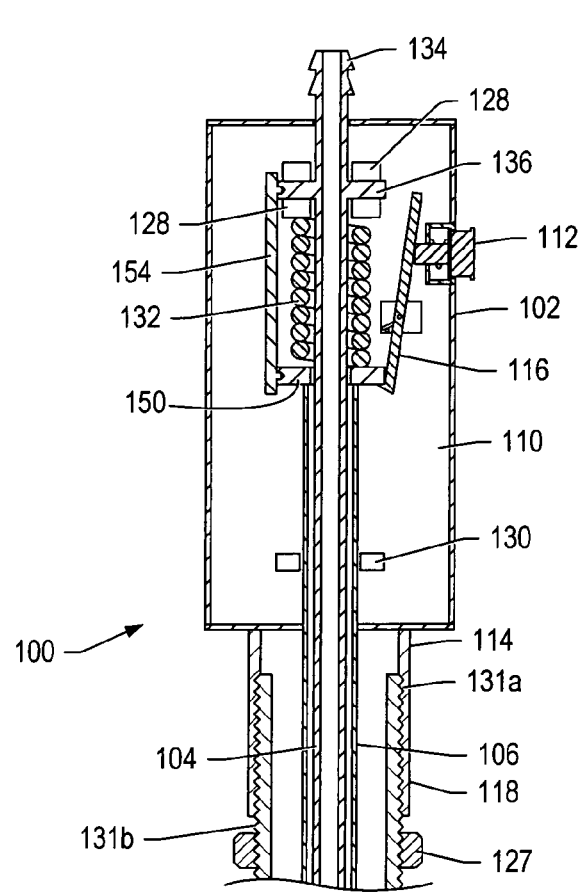
FIG. 2A depicts a cross-sectional representation of a proximal portion of an embodiment of an actuator of a biopsy needle assembly.
Figure 2B:
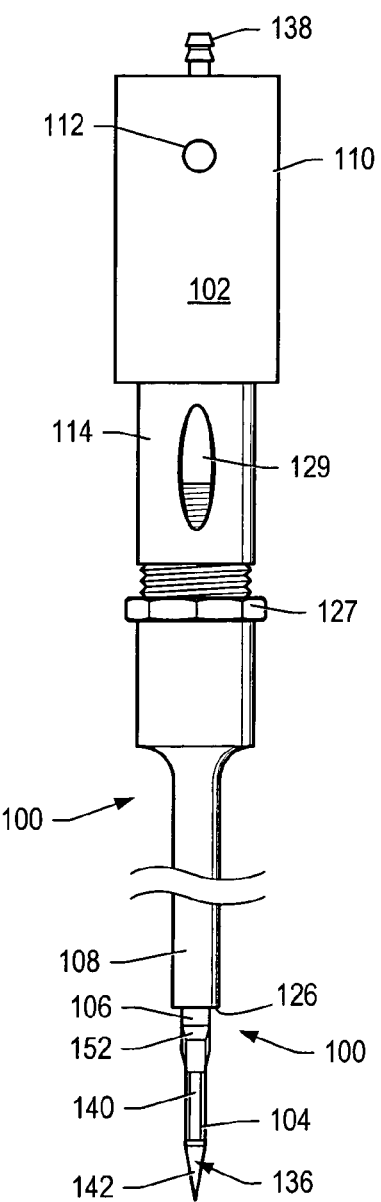
FIG. 2B depicts a side representation of an embodiment of a biopsy needle assembly.

In some actuator embodiments, a sheath extension is a non-adjustable portion of an actuator body. In other actuator embodiments, a position of the sheath extension relative to an actuator body may be adjustable. For example, the actuator body may include a female threaded opening 131a that mates with male threading 131b of the sheath extension. The sheath may be threaded into or out of the actuator body to adjust the position of the sheath extension as depicted in FIG. 2A. A lock ring 127 may be placed on the sheath extension threading as depicted in FIG. 2A. The lock ring may be threaded against the actuator body after the sheath extension is at a desired position to inhibit further movement of the sheath extension relative to the actuator body. The ability to change the position of the sheath extension may allow for control of the distance that the sample needle will extend beyond the end of the sheath when a detent of the actuator is placed in a second sheath opening of the sheath. The actuator body may include a window 129 that allows the end of the position sleeve to be observed as depicted in FIG. 2B. The body of the sleeve may also include a scale that indicates how much farther the sample needle is extended beyond a standard (or zero) extension.

Actuator 102 provides a driving force that moves sample needle 104 relative to cutter 106. In some actuator embodiments, such as the embodiment depicted in FIG. 2, a portion of sample needle 104 may be fixedly coupled to actuator 102 to inhibit longitudinal movement of the sample needle relative to the actuator. Actuator 102 moves cutter 106 when the actuator is activated. In some actuator embodiments, a cutter is fixedly coupled to the actuator and the actuator moves a sample needle when the actuator is activated. In other actuator embodiments, the actuator moves both a sample needle and a cutter when the actuator is activated. For example, activation of the actuator may move the cutting end of a cutter away from the actuator and simultaneously retract a needle portion of a sample needle towards the actuator. The driving force used to move a sample needle and/or a cutter may be spring driven (shown in FIG. 2), motor driven, hydraulically driven and/or driven by compressed gas.

Actuator 102 may include sample needle retainers 128, cutter stop 130 and/or drive mechanism 132. Sample needle retainers 128 may inhibit longitudinal movement of sample needle 104 relative to actuator 102. Cutter stop 130 may be a contact surface that engages a stop portion of cutter 106 to limit a range of longitudinal movement of the cutter. Drive mechanism 132 may move cutter 106 when release 112 is activated. In some biopsy needle assembly embodiments, a drive mechanism may be coupled to an actuator body, a sample needle and/or a cutter. In other biopsy needle assembly embodiments, a drive mechanism may be coupled to a sample needle and a cutter. Drive mechanism 132 may be a spring or elastic member that expands and forces the stop portion of cutter 106 to cutter stop 130 when release 112 is activated. Activating release 112 may move lever arm 116 that engages the stop portion of cutter 106 so that the drive mechanism moves the stop portion of cutter 106 to cutter stop 130. In some actuator embodiments, a torsion spring may return the lever arm to an initial position.

Sample needle 104 of a biopsy needle assembly embodiment may include connector 134 and retainer 136. Sample needle retainer 136 may be a ring that fits within sample needle retainers 128 of actuator 102. When retainer 136 is positioned in sample needle retainers 128 of actuator 102, longitudinal movement of sample needle 104 relative to the actuator may be inhibited.

FIG. 3 depicts a cross-sectional representation of an embodiment of a distal portion of a biopsy needle assembly. Needle portion 138 of sample needle 104 may be inserted into tissue to be sampled during use of biopsy needle assembly 100. Needle portion 138 may include sample opening 140 and tip 142. When needle portion 138 is inserted into tissue, a portion of the tissue may be seated in sample opening 140. Sample opening 140 may have a length that allows a tissue sample to seat within the sample opening. In some embodiments, the length of sample opening 140 is between about 5 millimeters (mm) and 20 millimeters. In an embodiment, the length of the sample opening is about 12 mm. Larger or smaller sample openings may be used to accommodate characteristics of tissue to be sampled. Tip 142 of needle portion 138 may be tapered to facilitate easy insertion of the needle portion into tissue. Tip 142 may be made of, or may include a coating of, hardened material to facilitate insertion of needle portion 138 into tissue.

In some sample needle embodiments, needle portion 138 may be hollow. The needle portion may be a modified 16–26 gauge needle. In an embodiment of a sample needle, a needle portion is a modified 21 gauge needle. Larger or smaller gauges of modified needles may also be used to accommodate tissue to be sampled. A vacuum may be drawn on the hollow portion of the needle to remove fluid from tissue and/or to seat a tissue sample in sample opening 140. In some embodiments, a vacuum may be drawn through sample needle 104. A vacuum source may be coupled to connector 134 (shown in FIG. 2). The vacuum source may be, but is not limited to, a syringe and plunger, a vacuum pump, an aspirator system and/or other pressure reduction system. Fluid removed from a patient by the vacuum source may be collected and analyzed if desired. In some biopsy needle assembly embodiments, sample needle 104 and/or needle portion 138 may not be hollow or may include a blocking portion that inhibits a vacuum from being drawn on fluid or tissue in the sample opening.

FIG. 4 depicts a cross-sectional representation of an embodiment of a distal portion of biopsy needle assembly 100. Sample needle 104 may include opening 144. After needle portion 138 is inserted into tissue, a vacuum may be drawn on cutter 106, through opening 144 and against fluid and/or tissue in sample opening 140 of sample needle 104. If a vacuum is drawn through cutter 106, a portion of sample needle 104 that is coupled to needle portion 138 may be solid instead of hollow. In some biopsy needle assembly embodiments, a vacuum may be drawn through a cutter in a space between a portion of a sample needle and the cutter. A cutter may include an opening and a connector that allows a vacuum source to be connected to the cutter. The sample needle may include one or more gaskets that contact an inner surface of the cutter. In some embodiments, such as the embodiment depicted in FIG. 4, a close tolerance between needle portion 138 and a cutting section of cutter 106 may eliminate the need for a gasket positioned between the needle portion and the cutter.

Figure 5:
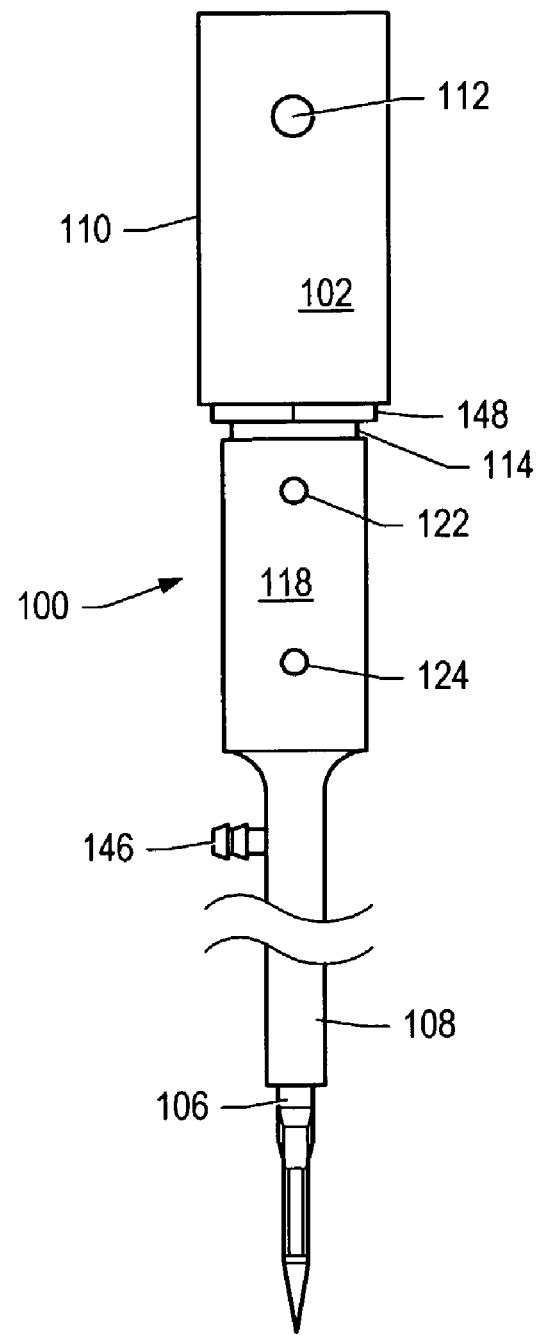
FIG. 5 depicts an embodiment of a biopsy needle assembly.

FIG. 5 depicts a side representation of an embodiment of a biopsy needle assembly that includes a connector through a sheath and into a cutter. Connector 146 may be used to draw a vacuum in a space between the cutter and the sample needle. Vacuum drawn on the connector may be directed through an opening in the sample needle so that the vacuum is directed to the sample opening. The biopsy needle assembly may include locking washer 148 on sheath connector 114. Locking washer 148 may allow a position of sheath connector 114 to be locked after adjustment of the sheath connector relative to body 110.

Referring to FIG. 1 and FIG. 2, cutter 106 of a biopsy needle assembly embodiment may include cutter retainer 150 and cutting edge 152. Cutter 106 may be positioned in actuator 102. Drive mechanism 132 may contact an upper surface of cutter retainer 150. In an initial position, drive mechanism 132 may be compressed and lever arm 116 may hold cutter retainer 150 stationary relative to body 110 of actuator 102. Activating release 112 may move lever arm 116 so that drive mechanism 132 moves cutter retainer 150 to actuator cutter stop 130. When cutter retainer 150 is positioned against actuator cutter stop 130, cutting edge 152 may extend past sample opening 140 of sample needle 104 so that cutter 106 separates a tissue sample positioned in the sample opening from adjacent tissue. In some cutter embodiments, cutting edge 152 may be angled relative to a longitudinal axis of the cutter to facilitate insertion of the cutting edge into tissue. Separating tissue with a cutter may eliminate a need to reciprocate a needle within tissue to collect a tissue sample.

Cutting edge 152 of cutter 106 may include a sharp edge that is able to separate a tissue sample positioned in sample opening 140 of sample needle 104 from adjacent tissue. Cutting edge 152 may be made of, or may include a coating of, a hardened material to facilitate insertion of the cutting edge into tissue. When cutter 106 is inserted into sheath 108 of a biopsy needle assembly embodiment, cutting edge 152 may be positioned against a portion of needle portion 140 of sample needle 104 to inhibit contact of the cutting edge with the sheath.

A portion of cutter 106 may be flexible to allow the cutter to follow a path through tissue or through an instrument towards tissue that is to be sampled. The flexible portion may have enough rigidity to allow cutter 106 to be inserted into tissue that is to be sampled. The flexible portion of cutter 106 may be a conduit. The conduit may be made of metal and/or polymer tubing. An inner surface of cutter 106 may be made of, or may include a coating of, material that reduces friction between the cutter and sample needle 104. Portions or all of inner surface of the cutter 106 may be made of, or may include a coating of, a fluorine-containing resin (e.g., TEFLON®) or similar material that has a low frictional coefficient. An outer surface of cutter 106 may be made of, or may include a coating of, material that reduces friction between tissue and/or between a sheath and the cutter.

Sheath 108 of a biopsy needle assembly embodiment may contain needle portion 138 of sample needle 104 and cutting edge 152 of cutter 106 as the biopsy needle assembly is inserted into a patient. Sheath 108 may inhibit needle portion 138 and cutting edge 152 from contacting tissue or an instrument as the biopsy needle assembly is inserted into the patient. Sheath 108 may be, or may include a layer of, aramid fibers such as KEVLAR®. When sheath 108 is inserted to a desired depth in the patient so that sheath end 126 is positioned adjacent to tissue that is to be sampled, the position of actuator 102 relative to the sheath may be adjusted so that needle portion 138 extends into the tissue to be sampled.

A portion of sheath 108 may be flexible to allow the sheath to follow a path through tissue or through an instrument towards tissue that is to be sampled. The flexible portion may have enough strength to inhibit puncture by cutting edge 152 of cutter 106 or by needle portion 138 of sample needle 104. Frictional forces between an instrument and a biopsy needle may inhibit easy movement of the biopsy needle relative to the needle. An inner surface of sheath 108 may be made of, or may include a coating of, material that reduces friction between cutter 106 and/or sample needle 104 and the sheath. An outer surface of sheath 108 may be made of, or may include a coating of, material that reduces friction between tissue and/or an instrument and the sheath. The sheath may include one or more layers of a fluorine-containing resin (e.g., TEFLON®) that has a low frictional coefficient.

In an embodiment of a biopsy needle assembly, sample needle 104, drive mechanism 132 and cutter 106 may be provided in a package as a sterilized, pre-assembled unit. As depicted in FIG. 2, holder 154 may couple sample needle retainer 136 to the cutter retainer 150 to maintain drive mechanism 132 in an initial position. Holder 154 may include protrusions. Sample retainer 136 may include an indention sized to hold a protrusion of the holder. Cutter retainer 150 may include an indention sized to hold a protrusion of the holder. Protrusions of holder 154 may be positioned in indentions in sample retainer 136 and cutter retainer 150. Holder 154 may be removed or cut, after which the lever arm 116 of actuator 102 holds cutter retainer 150 in place.

A portion of sample needle 104 may be flexible to allow the sample needle to follow a path through tissue or through an instrument towards tissue that is to be sampled. The flexible portion may have enough rigidity to allow needle portion 138 to be inserted into tissue that is to be sampled. The flexible portion of sample needle 104 may be a conduit. The conduit may be made of metal and/or polymer tubing. Portions of the sample needle may be made of, or may include a coating of, material that reduces friction between the sample needle and cutter 106. Portions or all of the sample needle may be made of, or may include a coating of, a fluorine-containing resin (e.g., TEFLON®) or similar material that has a low frictional coefficient.

In some biopsy needle assembly embodiments, a cap may cover needle portion 138 of sample needle 104 and cutting edge 152 of cutter 106 to inhibit contact of the cutting edge and/or needle portion with people or objects. The cap may be sized to fit within sheath 108 so that needle portion 138 and cutting edge 152 can be easily inserted into the sheath without the needle portion and cutting edge contacting the sheath during insertion into the sheath.

To form a biopsy needle assembly embodiment, a new sample needle, drive mechanism and cutter may be removed from a package. An actuator body may be opened. If a sample needle, a drive mechanism and a cutter are currently positioned in the actuator, the components may be removed to provide room for insertion of the new components. Pressure may be applied to a release of the actuator to move a lever arm of the actuator to a released position. A sample needle retainer may be positioned in sample needle retainers of the actuator. A portion of the sample needle may be placed in a channel in a cutter stop. Pressure on the release may be removed to allow an engager portion of the lever arm to contact a cutter retainer. A holder that maintains the drive mechanism in an initial position may be removed from the sample needle retainer and the cutter retainer. The actuator body may be closed. The actuator body may include a snap lock, threaded connection, or other type of fastening system that holds the body in a closed position.

A cap covering a needle portion of the sample needle and a cutting edge of the cutter may be inserted into the sheath until the cap extends beyond a distal end of the sheath. The cap may be removed from the needle portion and the cutting edge. The actuator may be positioned in an initial position relative to the sheath so that the needle portion and the cutting edge are retracted into the sheath to form a biopsy needle assembly that is ready for use.

In some biopsy needle assembly embodiments, a sample needle, a drive mechanism, a cutter and a sheath may be provided as a unit for connection to an actuator. The unit may not include a cap over a needle portion of the sample needle and cutting portion of the cutter. A removable holder may fix the position of the sheath relative to the cutter. The removable holder may be, but is not limited to, tape, a screw, a pin or adhesive.

In some biopsy needle assembly embodiments, portions of a sample needle, a drive mechanism and portions of a cutter may be positioned in a sealed actuator. A reset assembly may allow the drive mechanism to be returned to an initial position after use of the biopsy needle assembly. For example, the cutter may include protrusions located near the actuator. A reset tool may contact the protrusions and allow the drive mechanism to be returned to an initial position after use of the biopsy needle assembly.

A needle portion of a sealed actuator may be removably coupled to the sample needle to allow the needle portion to be removed after a tissue sample is taken. A new needle portion may be attached to the sample needle to allow another tissue sample to be taken. A portion of the cutter that includes a cutting edge may be removably coupled to the cutter to allow the cutting edge to be replaced, if necessary.

Figure 8:
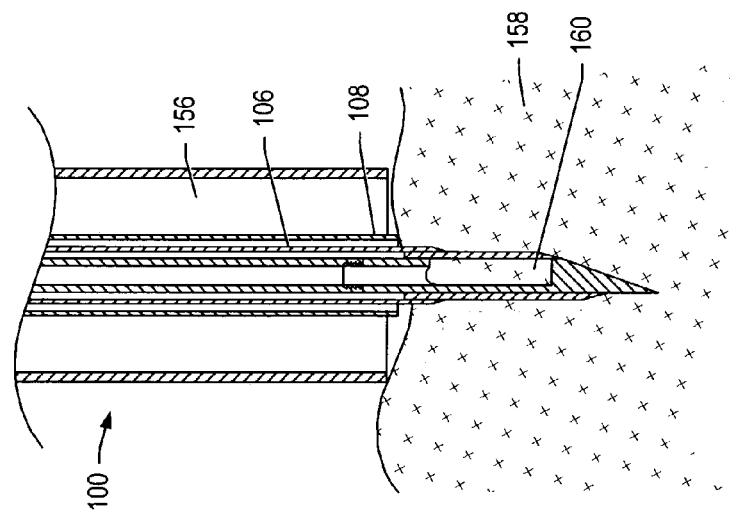
FIG. 8 depicts a cross-sectional representation of a portion of a biopsy needle assembly embodiment after a cutter has separated a tissue sample.
Figure 7:
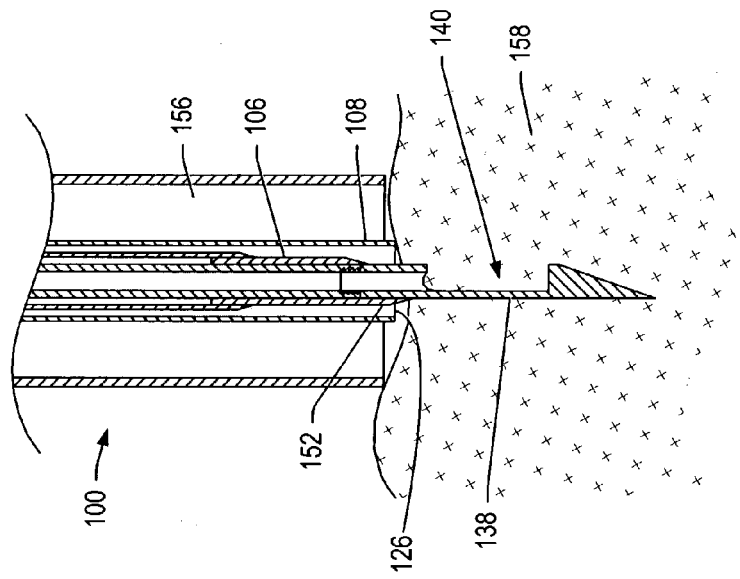
FIG. 7 depicts a cross-sectional representation of a portion of a biopsy needle assembly embodiment after insertion of a needle portion into tissue.
Figure 6:
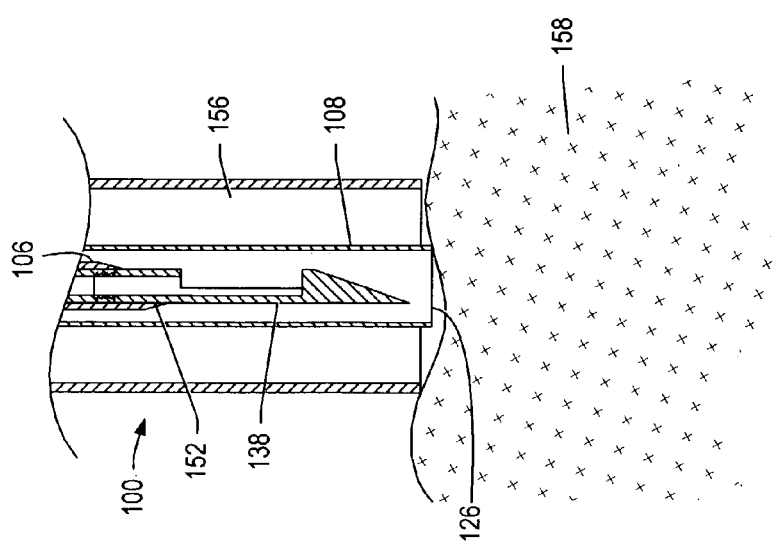
FIG. 6 depicts a cross-sectional representation of a portion of a biopsy needle assembly embodiment prior to insertion of a needle portion into tissue.

FIG. 6, FIG. 7 and FIG. 8 depict cross-sectional representations of portions of a biopsy needle assembly embodiment during use. Sheath 108 of biopsy needle assembly 100 is inserted into instrument 156. Instrument 156 may be an endoscope, medical device insertion instrument or other instrument that includes a conduit or channel able to serve as a guide to position sheath end 126 adjacent to tissue to be sampled. The conduit or channel of instrument 156 may be flexible or rigid.

In some embodiments, cutting edge 152 of cutter 106 and needle portion 138 of sample needle 104 are positioned in sheath 108 during insertion of the sheath into instrument 156. In an alternative embodiment, cutting edge 152 and needle portion 138 are inserted into sheath 108 after the sheath is positioned in instrument 156.

Sheath 108 may be positioned at a desired location in tissue 158 of a patient and/or in instrument 156. A position of sheath 108 may be monitored using fluoroscopic imaging and/or other imaging techniques. Sheath 108 may be reciprocated relative to instrument 156 until the desired location is achieved. FIG. 6 depicts sheath 108 in instrument 156 positioned adjacent to tissue that is to be sampled.

After positioning sheath 108, needle portion 138 may be extended from sheath end 126 into tissue 158 that is to be sampled. FIG. 7 depicts needle portion 138 extended beyond sheath end 126. The position of needle portion 138 may be monitored using fluoroscopic imaging and/or other imaging techniques. Needle portion 138 may be reciprocated relative to sheath 108 until the needle portion is properly positioned in tissue 158. In an embodiment of biopsy needle assembly 100, such as the biopsy needle assembly embodiment depicted in FIG. 1, needle portion 138 is extended from sheath end 126 by depressing detent 120 of actuator 102 and moving the actuator until the detent engages opening 124 in sheath 108.

After needle portion 138 is positioned at the desired location in tissue 158, a vacuum source may be coupled to biopsy needle assembly 100 to seat a tissue sample within sample opening 140. After seating tissue in sample opening 140, release 112 (shown in FIG. 1) of actuator 102 (shown in FIG. 1) may be activated to move cutter 106 relative to needle portion 138 so that tissue in the sample opening is separated from tissue 158 to form tissue sample 160. FIG. 8 depicts biopsy needle assembly 100 after tissue sample 160 has been formed by cutter 106.

After tissue sample 160 is formed, biopsy needle assembly 100 may be removed from instrument 156. In a biopsy needle assembly embodiment, such as the embodiment depicted in FIG. 1, detent 120 may be depressed and actuator 102 may be withdrawn so that the detent is positioned in opening 122 of sheath 108. Sheath 108 and the rest of biopsy needle assembly 100 may be removed from instrument 156 and the patient. If desired, a new sample needle, cutter and/or sheath may be coupled to the biopsy needle assembly, inserted into an instrument and another tissue sample may be taken. Alternatively, actuator 102, cutter 106 and sample needle 104 may be removed as a unit from sheath 108 and the patient while leaving the sheath in instrument 156. The actuator may be fitted with a new cutter, drive mechanism and sample needle unit for insertion into the sheath to take an additional tissue sample.

After removing cutter 106 and sample needle 104 from the patient, tissue sample 160 may be removed from sample opening 140. In an embodiment, a portion of cutter 106 and sample needle 104 near needle portion 138 may be severed from other portions of the cutter and sample needle. A portion of cutter 106 that includes cutting edge 152 may be removed from sample needle 104 to expose tissue sample 160. Tissue sample 160 may be removed and subjected to testing. In some biopsy procedures, a sample needle, a drive mechanism and a cutter with a tissue sample positioned in the sample needle may be sent as a unit to a laboratory that is to test the tissue sample. Personnel at the laboratory may remove the tissue sample from the sample needle.

An embodiment of a biopsy needle assembly may advantageously be able to follow a pathway through tissue and/or an instrument to tissue that is to be sampled. Portions of a biopsy needle assembly may be flexible to allow the biopsy needle assembly to be used with a flexible instrument.

A biopsy needle assembly may advantageously eliminate a need to reciprocate a needle to obtain a tissue sample. A biopsy needle assembly may be used to take a tissue sample from relatively hard tissue because a needle portion of the biopsy needle assembly only needs to be inserted into the tissue one time. Elimination of reciprocation to take a tissue sample may improve the quality and quantity of a tissue sample taken during a biopsy procedure. Elimination of reciprocation may improve reproducibility and consistency of tissue samples taken during biopsy procedures.

An embodiment of a biopsy needle assembly may include a needle portion made of material that may be observed using fluoroscopic and/or other imaging techniques. A portion of the sheath may also include material that may be observed using fluoroscopic and/or other imaging technique. In some biopsy procedures, a position of the needle portion may be observed prior to taking a tissue sample to ensure that the needle portion is in the tissue that is to be sampled.

An embodiment of a biopsy needle assembly may advantageously allow a vacuum to be drawn on tissue to be sampled to ensure that a sample is seated within a sample opening of the biopsy needle assembly. Further advantages of biopsy needle assemblies may be that the biopsy needle assemblies are sturdy, durable, lightweight, simple, efficient, economical, safe and reliable. The biopsy needle assemblies may also be easy to manufacture and use.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A biopsy device comprising:
    a cutter;
    a sample needle, wherein at least part of the sample needle is positionable in the cutter;
    an actuator coupled to the cutter and to the sample needle, wherein the actuator is configured to alter a spatial relationship between the cutter and the sample needle such that a tissue sample in a sample opening of the sample needle is separated from adjacent tissue by a cutting edge of the cutter; and
    a sheath comprising a threaded portion, wherein the threaded portion of the sheath is positionable in a threaded opening in the actuator, and wherein the position of the sheath relative to the actuator is adjustable by threading the sheath into or out of the threaded opening, and wherein the cutter and the sample needle are positionable in the sheath;
    wherein at least a portion of the biopsy device is flexible such that the biopsy device is positionable in an endoscope during use.

2. The biopsy device of claim 1, wherein at least a portion of the cutter is flexible.

3. The biopsy device of claim 1, further comprising a lock ring, wherein the lock ring is configured to inhibit movement of the sheath relative to the actuator after the sheath is in a desired position.

4. The biopsy device of claim 1, wherein an end of the cutter is tapered to facilitate insertion of the cutter into tissue.

5. The biopsy device of claim 1, wherein at least a portion of the sample needle is flexible.

6. The biopsy device of claim 1, wherein an end of the sample needle is tapered to facilitate insertion of the sample needle into tissue.

7. The biopsy device of claim 1, wherein the sample needle comprises a connector configured to couple to a vacuum source.

8. The biopsy device of claim 1, wherein the cutter comprises a connector configured to couple to a vacuum source.

9. The biopsy device of claim 1, wherein the cutting edge and the sample needle are positioned in the sheath when the actuator is in a first position relative to the sheath, and wherein a needle portion of the sample needle is extended beyond an end of the sheath when the actuator is in a second position relative to the sheath.

10. The biopsy device of claim 1, wherein the sample needle comprises a section of hardened material to facilitate insertion into tissue.

11. The biopsy device of claim 1, wherein the cutting edge comprises a section of hardened material to facilitate insertion into tissue.

12. The biopsy device of claim 1, wherein the actuator comprises a window, and wherein an end of the sheath is viewable through the window.

13. The biopsy device of claim 1, further comprising a cutter stop comprising a surface that engages a portion of the cutter, wherein the cutter stop is configured to limit a range of longitudinal movement of the cutter.

14. The biopsy device of claim 1, wherein the sample needle comprises one or more retainers configured to engage one or more retainers of the actuator.

15. The biopsy device of claim 1, wherein the actuator comprises a drive mechanism coupled to the sample needle and the cutter, and wherein the drive mechanism is configured to move the cutting edge relative to the sample needle to separate the tissue positioned in the sample opening from the adjacent tissue.

16. The biopsy device of claim 15, wherein the drive mechanism comprises a spring.

17. The biopsy device of claim 15, wherein the drive mechanism comprises a motor.

18. The biopsy device of claim 15, wherein the drive mechanism comprises compressed air.

19. The biopsy device of claim 15, wherein the drive mechanism comprises a hydraulic system.

20. The biopsy device of claim 1, wherein at least a portion of the sample needle is hollow, and further comprising a vacuum source coupled to the sample needle, wherein a vacuum is drawn in the hollow portion of the sample needle such that fluid is collected through the sample needle during use.

21. A method comprising:
providing a sheath comprising a sample needle positioned in a cutter;
positioning a threaded portion of the sheath in a threaded opening of an actuator;
adjusting a position of the sheath relative to the actuator by threading the sheath into or out of the threaded opening;
positioning at least a portion of the sheath and the actuator in an endoscope;
positioning the endoscope in a body lumen, wherein a distal end of the endoscope is adjacent tissue to be sampled;
positioning a distal end of the sheath adjacent the distal end of the endoscope;
placing a sample opening of the sample needle in the tissue to be sampled; and
activating the actuator such that the actuator moves a cutter relative to the sample needle to separate tissue in the sample opening from adjacent tissue.

22. The method of claim 21, further comprising reducing air pressure within the sample opening to facilitate positioning of the tissue to be sampled in the sample opening.

23. The method of claim 21, further comprising engaging a lock ring with the actuator to inhibit movement of the actuator with respect to the sheath after the sheath is at a desired position.

24. The method of claim 21, further comprising determining a position of the sheath relative to the actuator through a window in the actuator.

25. The method of claim 21, further comprising engaging a surface with a stop portion of the cutter to limit longitudinal movement of the cutter relative to the sample needle by the actuator.

26. The method of claim 21, further comprising
drawing a vacuum in a hollow portion of the sample needle; and
collecting fluid proximate the tissue being sampled with the sample needle.

27. The method of claim 26, further comprising analyzing the collected fluid.

28. The method of claim 21, further comprising
inhibiting the sample needle and the cutter from contacting the endoscope and/or tissue during initial positioning of the sheath in the endoscope.

* * * * *